United States Patent [19]

Maurer

[11] Patent Number: 4,653,479
[45] Date of Patent: Mar. 31, 1987

[54] INTERRUPTED DRIVE LIMB MOTION APPARATUS

[75] Inventor: Donald D. Maurer, Anoka, Minn.

[73] Assignee: Empi, Inc., Fridley, Minn.

[21] Appl. No.: 692,178

[22] Filed: Jan. 17, 1985

[51] Int. Cl.$^4$ ............................................. A61H 1/00
[52] U.S. Cl. .............................. 128/25 B; 128/423 W
[58] Field of Search .......... 128/421, 422, 423, 423 W, 128/25 R, 25 B, 26

[56] References Cited

U.S. PATENT DOCUMENTS

| 1,498,529 | 6/1924 | Allen | 128/421 |
| 4,256,095 | 3/1981 | Graham | 128/24.1 |
| 4,392,496 | 7/1983 | Stanton | 128/423 W |
| 4,509,509 | 4/1985 | Bouvet et al. | 128/25 R |

Primary Examiner—Leo P. Picard
Attorney, Agent, or Firm—Kinney & Lange

[57] ABSTRACT

An apparatus for mobilization of a human limb includes a carriage for supporting the limb through a range of angular movement and a carriage drive which provides an interrupted drive force to the carriage in the form of alternating drive and pause periods. A stimulation device applies electrical stimulation to muscles of the limb intermittently and in a predetermined temporal relationship to the drive and pause periods. The apparatus makes possible a dithered or vibratory movement of the limb, rather than continuous motion, and offers a wide range of therapeutic modes.

12 Claims, 3 Drawing Figures

INTERRUPTED DRIVE LIMB MOTION APPARATUS

BACKGROUND OF THE INVENTION

1. Field of the Invention

This invention relates to apparatus for mobilizing of human limbs.

2. Description of the Prior Art

In recent years, there has been an increasing awarness of the advantages of mobilization of human joints as a part of the orthopedic care which follows an injury, an illness, or a surgical procedure. A joint can stiffen rapidly as a result of the immobilization, and in many cases extensive therapy is required in order to regain full use of the joint after it has stiffened. In the rehabilitation of human joints, therefore, it has been found useful to keep those joints mobilized by means of a device that continuously forces the limb to move, slowly and over a period of many hours.

Devices that perform this function have been developed and are commercially available. These devices, which are usually referred to as "continuous passive motion" (CPM) devices consist generally of a motorized frame or carriage in which the affected limb is held by gravity or by straps, and a control circuit that enables the clinician to start and stop the device, to adjust its speed, and to determine the extent of the motion by setting a maximal flexion and a maximal extension position.

Various forms of muscle stimulation have also been developed for therapeutic purposes in the treatment of limbs and joints. Both direct muscular stimulation and neuromuscular stimulation (NMS) have been used.

Direct muscular stimulation describes the action upon a living muscle or group of muscles by an extraneous agent for the purpose of causing said muscle or group of muscles to contract. This is particularly useful in those cases in which the muscle or group of muscles cannot fully or partially contract because of disease or trauma. The extraneous agent can be a chemical substance, a mechanical, thermal, or electrical impulse, or any other action that will interact directly with the contractible fibers and cause them to contract. In the context of the present application direct muscular stimulation is construed to mean electrical muscular stimulation because stimulation of muscle tissue is best and most controllably achieved by means of pulses of electric potential applied in the vicinity of the muscle or group of muscles one wishes to stimulate. In any embodiment of this invention in which direct muscular stimulation is called for, electrical muscle stimulation preferably will be employed.

Neuromuscular stimulation is the indirect stimulation of muscles or groups of muscles effected through the mediation of those nerve fibers that innervate them. Obviously, neuromuscular stimulation can only occur when the muscle or group of muscles one wishes to act upon is innervated, i.e. at least some of the nerve fibers that are normally connected to it are intact and the connection is viable. The advantage of neuromuscular stimulation over direct muscular stimulation is that nerve fibers have a lower stimulation threshold and thus neuromuscular stimulation can be effected with lower energies and more easily. Many chemical and physical actions can effect neuromuscular stimulation, but electrical neuromuscular stimulation is preferred because of the precision and ease with which an electric potential pulse can affect a nerve. In the context of this application, electrical neuromuscular stimulation preferably is meant whenever neuromuscular stimulation is referred to as part of an embodiment of this invention.

The concept has been introduced of coupling a neuromuscular stimulation (NMS) device to a CPM device, thus providing what has been called "continuous active motion" (CAM). The clinician thus has the option of either moving the limb passively with a motorized device, or making the limb move autonomously by causing the limb's muscles to contract, or to do both. In a copending patent application entitled "NMS Aided Continuous Passive Motion Apparatus" by T. C. Wright and S. H. Ober, Ser. No. 578,470, filed Feb. 9, 1984, which is assigned to the same assignee as the present application, a system is shown in which the CPM carriage is paused when maximal extension is reached. The NMS device is then turned on for several seconds and, after that, movement of the CPM carriage back toward maximal flexion resumes.

The technology of CPM and CAM, once accepted by the medical profession and implemented with convenient and economical apparatus, is not limited to the mobilization of diseased or traumatized joints. There is evidence reported in the literature that CPM improves the circulation of blood in the affected limb and prevents venous stasis and thrombosis. It can also be inferred that CPM and CAM may be beneficial in the as yet unexplored cure and prevention of several afflictions of bone, tendons, muscles and other structures of human limbs.

SUMMARY OF THE INVENTION

The present invention is an improved apparatus for mobilization of a human limb which provides a wide range of therapeutic modalities. In the apparatus of the present invention, a carriage drive means is caused to provide an interrupted drive during angular movement of the carriage between the maximal flexion and maximal extension positions. This interrupted drive is preferably in the form of alternating drive and pause periods.

The interrupted drive refers to the motion of the drive apparatus (e.g. a motor and associated gears and linkages), and no inference is made as to the actual state of the limb during the pause period. Thus, depending on the action of gravity, on the geometric and dynamic relationship between the limb and the carriage, and on other factors, in the pause period the limb may either (a) stop its motion entirely and remain immobile, or (b) continue its motion as if by inertia, or (c) reverse its motion, so as to resume in the subsequent drive period from a position that it had already reached in the previous drive period.

In addition, in preferred embodiments of the present invention a stimulation means applies electrical stimulation to muscles of the limb (either directly or indirectly). The operation of the stimulation means is coordinated with the operation of the drive means so that stimulation periods during which electrical stimulation is applied have a predetermined temporal relationship to the drive and pause periods of the interrupted drive of the carriage.

In preferred embodiments of the present invention, the apparatus includes means for selecting time durations of the drive, pause and stimulation periods, as well as a phase relationship between these periods.

The present invention makes possible a dithered or vibratory movement of the limb, rather than continuous motion used in the prior art. This dithered or vibratory motion (which is superimposed upon the general reciprocal movement of the limb produced by the carriage) is believed to offer significant advantages over the uninterrupted continuous passive motion used in prior art CPM devices.

DETAILED DESCRIPTION OF THE PREFERRED EMBODIMENTS

Figure 1:
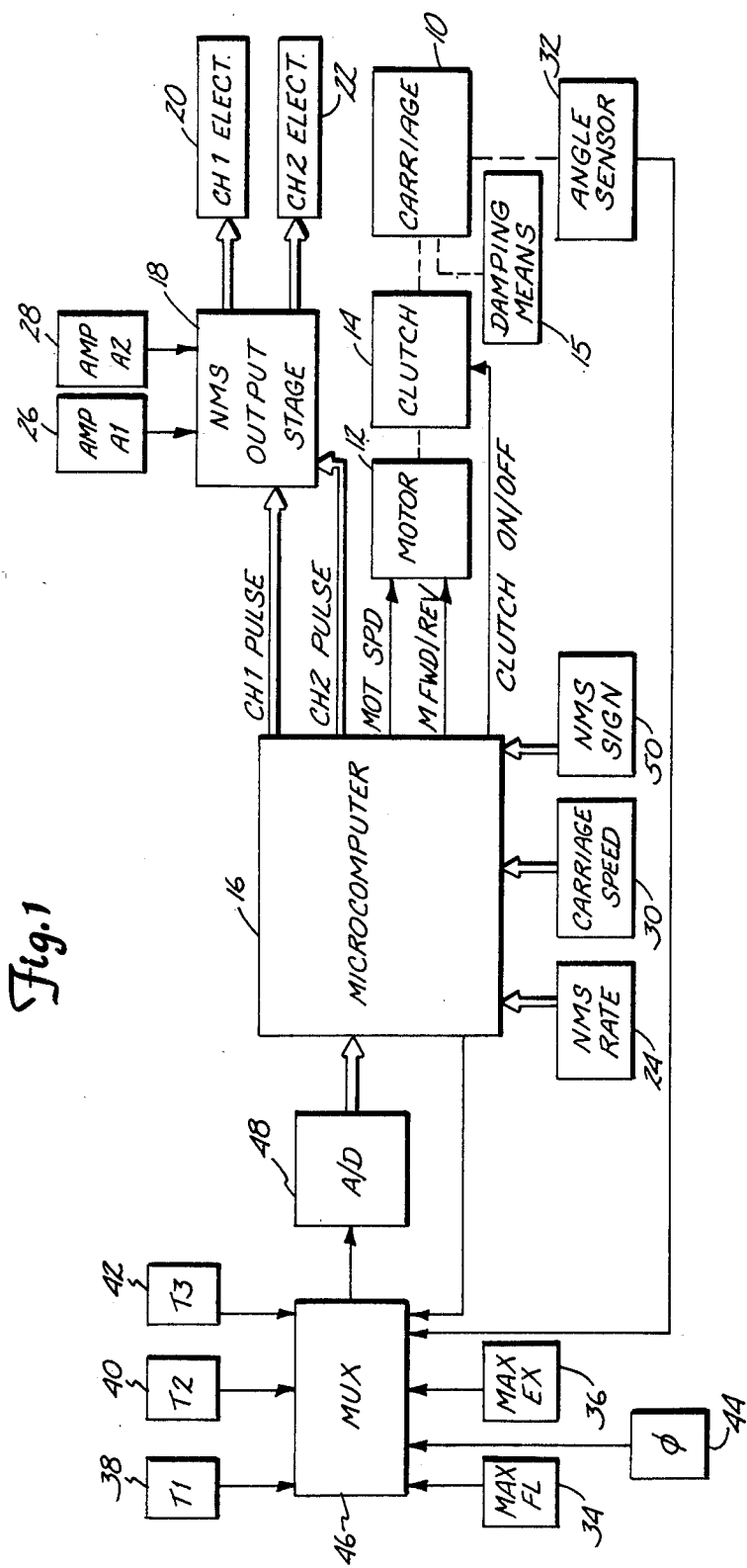
FIG. 1 is an electrical block diagram of a preferred embodiment of the present invention.

The block diagram shown in FIG. 1 illustrates a preferred embodiment of the present invention, in which therapy for a limb of a patient is provided by interrupted drive coordinated with neuromuscular stimulation. The apparatus shown in FIG. 1 includes carriage 10, motor 12, clutch 14, damping means 15, microcomputer 16, NMS output stage 18, Channel 1 electrodes 20, Channel 2 electrodes 22, NMS rate selector 24, Channel 1 and Channel 2 amplitude potentiometers 26 and 28, carriage speed selector 30, angle sensor 32, maximal flexion angle selector 34, maximal extension angle selector 36, drive time (T1) selector 38, pause time (T2) selector 40, NMS ON time (T3) selector 42, phase ($\phi$) selector 44, multiplexer 46, analog-to-digital (A/D) converter 48, and NMS sign selector 50.

Carriage 10 supports the limb of the patient and is driven by motor 12 through clutch 14. In one embodiment, carriage 10 is similar to the CPM carriage described in the previously mentioned application Ser. No. 578,470, and that description is incorporated by reference. It should be understood, however, that the present invention is not limited to a particular type of carriage.

In the embodiment shown in FIG. 1, microcomputer 16 controls both the speed and direction of motor 12, and also controls whether clutch 14 is engaged or disengaged based upon the selected carriage speed and the inputs from A/D converter 48. As a result, carriage 10 can move in either of two directions, and can be selectively connected and disconnected from motor 12, all under the control of microcomputer 16.

Two channels of neuromuscular stimulation are provided by NMS output stage 18 through Channel 1 electrodes 20 and Channel 2 electrodes 22, which are applied to the patient's limb. In the embodiment shown in FIG. 1, microcomputer 16 produces CH1 PULSE and CH2 PULSE signals which are supplied to NMS output stage 18. The pulse rate of the CH1 and CH2 PULSE signals are determined by an NMS rate input supplied to microcomputer 16 by NMS rate selector 24. The Channel 1 output signal produced by NMS output stage 18 and supplied to Channel 1 electrodes 20 is a function of the CH1 PULSE signal from microcomputer 16 and the amplitude control signal received from Channel 1 amplitude potentiometer 26. Similarly, the Channel 2 output signal supplied by NMS output stage 18 to Channel 2 electrodes 22 is a function of the CH2 PULSE signal from microcomputer 16 and the amplitude control signal from Channel 2 amplitude potentiometer 28.

In a preferred embodiment of the present invention, Channel 1 electrodes 20 are attached to the limb of a patient so that they provoke extension of the limb when activated. The Channel 2 electrodes 22, on the other hand, are attached to the limb so as to provoke flexion of the limb when activated.

Through coordinated operation of motor 12, clutch 14, and NMS output stage 18, therefore, both passive motion and active motion, in various combinations, can be achieved. The operator selected inputs provided by maximum flexion selector 34, maximum extension selector 36, and the T1, T2, T3 and and $\phi$ selectors 38, 40, 42 and 44 allow the physician, therapist or other medical personnel to select a program of carriage motion and NMS stimulation which provides a wide range of therapeutic modalities. Microprocessor 16 acts on NMS output stage 18 to turn on and off bursts of neuromuscular stimulation to either the Channel 1 electrodes 20 or the Channel 2 electrodes 22 at a preset intensity and pulse rate. The particular channel selected depends upon the direction of movement of carriage 10 and the desired sign relationship of the NMS stimulation to the direction of movement as selected by NMS sign selector 50.

In addition, microcomputer 16 acts on the drive of carriage 10 by engaging and disengaging clutch 14, thus halting or reinstating the motorized motion of carriage 10 at any time. Instead of, or in addition to acting on clutch 14, microcomputer 16 can also act directly on motor 12 to start and stop motor 12, or to reverse its direction of motion.

When clutch 14 is disengaged, carriage 10 is disconnected from drive force provided by motor 12. The limb and carriage 10 being then subject only to the force of gravity, damping means 15 (which preferably is formed by a suitable arrangement of springs connected to carriage 10) prevents the limb and carriage 10 from collapsing and maintains the attitude of the limb and carriage 10 while allowing a change in the motion imparted by the motor drive. In other words, the motion of carriage 10 can either continue by inertia, or can continue through the action of NMS, or it can be stopped (and even reversed) through the action of NMS. When clutch 14 is engaged, the motion of motor 12 caused by microcomputer 16 takes over and drives carriage 10 at the desired speed and in the desired direction.

TABLE 1 illustrates seven different combinations of active and passive motion which can be achieved under the control of microcomputer 16 by selective operation of motor 12, clutch 14 and NMS output stage 18. In TABLE 1, movement toward extension of the limb is designated as positive (+) and forward (FWD), while movement toward flexion is designated as negative (−) and reverse (REV).

TABLE 1

| MOTOR FWD/REV | CLUTCH ON/OFF | CARRIAGE DRIVE | CH1 NMS | CH2 NMS | ACTIVE/(A) PASSIVE/(P) |
|---|---|---|---|---|---|
| FWD | ON | FWD | ON | OFF | P + A |

TABLE 1-continued

| MOTOR FWD/REV | CLUTCH ON/OFF | CARRIAGE DRIVE | CH1 NMS | CH2 NMS | ACTIVE/(A) PASSIVE/(P) |
|---|---|---|---|---|---|
| FWD | ON | FWD | OFF | ON | P − A |
| REV | ON | REV | ON | OFF | −P + A |
| REV | ON | REV | OFF | ON | −P − A |
| EITHER | OFF | FREE | ON | OFF | +A |
| EITHER | OFF | FREE | OFF | ON | −A |
| EITHER | OFF | FREE | OFF | OFF | 0 |

Figure 2:
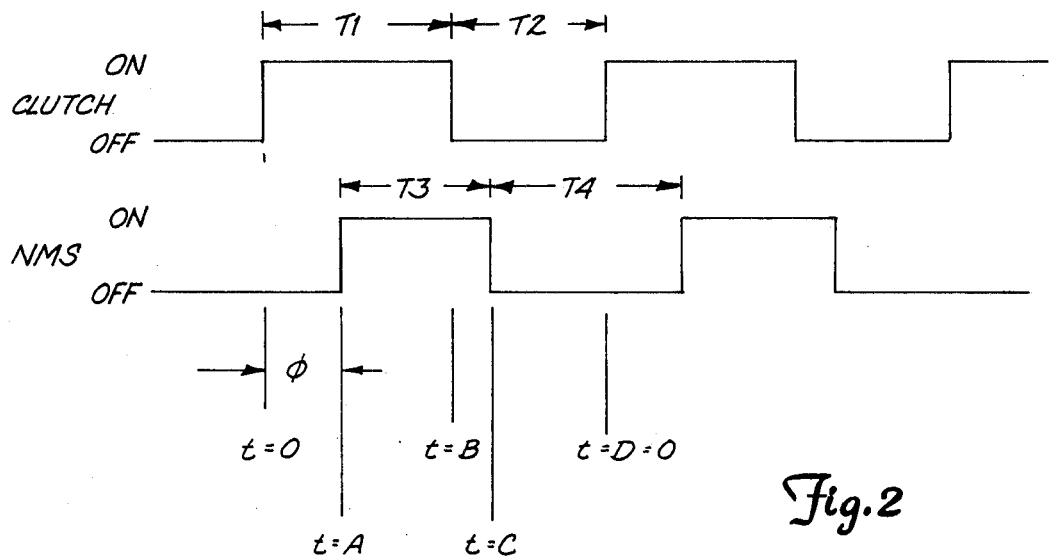
FIG. 2 is a diagram showing the relationship between the drive force supplied to the carriage and neuromuscular stimulation used in one embodiment of the present invention.

FIG. 2 illustrates one of many possible modes of operation of the system of FIG. 1. As shown in FIG. 2, clutch 14 is engaged for time interval T1 and then is disengaged for time interval T2, after which the cycle is started again.

During time interval T3, NMS is activated so as to either continue the motion, or stop it, or reverse it, depending upon the direction of motion of the carriage, and the particular electrodes 20 or 22 which are activated. NMS is applied for time interval T3, after which it is turned off and kept off for a time interval T4. In the particular embodiment illustrated in FIG. 2, $T1+T2=T3+T4$. This maintains a constant phase relationship $\phi$ between the beginning of carriage motion ON ($t=0$) and the beginning of NMS ON ($t=A$).

The effect of the relationship of carriage motion and NMS activation shown in FIG. 2 is to provide passive motion only (from $t=0$ to $t=A$), passive plus active motion (from $t=A$ to $t=B$), active motion only (from $t=B$ to $t=C$), and no propulsive force at all (from $t=C$ to $t=D=0$) during each cycle. This regimen can be maintained throughout an entire operating cycle from maximal flexion through maximal extension, and back to maximal flexion. In other embodiments of the present invention, the regimen can be varied so that, for example, there is one regimen when carriage 10 is moving from flexion to extension, and another regimen when moving from extension back to flexion. In still other embodiments, the regimen varies as a function of location within the cycle (e.g., NMS intensity or rate varied as a function of joint angle), or may be limited to only a portion of the cycle such as near the maximal extension and maximal flexion end points.

With the present invention, the range of available variables is virtually unlimited. T1, T2, T3, T4 and $\phi$ can be varied from very short duration (on the order of 0.05 seconds) to very long duration (on the order of minutes). In addition, the relationships of the variables and their relationship to the flexion/extension cycle is also selectable. This allows a wide range of therapeutic modalities and greater flexibility in the treatment program used by the physician or therapist.

One particularly advantageous use of the system of the present invention is in providing "dithered" motion of the limb. Dithered motion preferably makes use of very frequent and very short pauses in drive (of less than about one second duration, such as for example ten pauses per second each of 0.05 second duration). In other words, to produce dithered motion, the pauses and actuations of the drive to carriage 10 are much shorter in duration than the total cycle time of a flexion/extension operating cycle of carriage 10.

It is believed that dithered motion, as opposed to the continuous motion used in the prior art, can promote better and faster healing of traumatized or surgically repaired joints. Dithered motion tends to overcome the natural adherence of wetted surfaces of the prosthesis and membranes in the knee. The vibratory or dithered motion reduces the chance of natural adherence of the surfaces (which normally will cause initial resistance to motion of the joint followed by a jerk in movement of the joint when the continued motion of the carriage finally overcomes the adherence).

In addition, the vibratory or dithered motion provides stimulation to the limb and joint which provides blood flow increase and the potential for pain relief. In the past, the pain associated with continuous passive motion has been major concern in the application of CPM therapy.

In addition, the application of bursts of NMS, timed to coincide with pauses of carriage drive or otherwise synchronized to bear a fixed temporal relationship to the beginning of each pause period can be used to enhance the therapeutic benefits provided by dithered motion.

Figure 3:
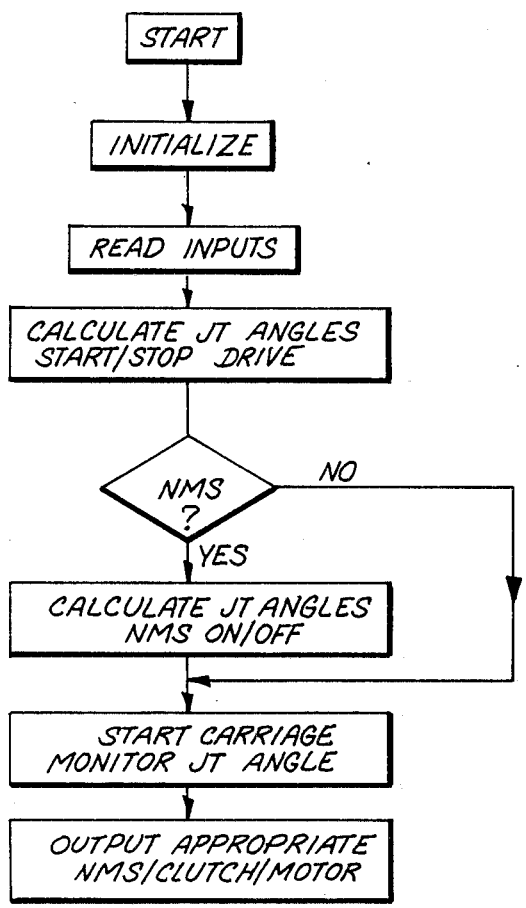
FIG. 3 is a flow chart illustrating operation of the microcomputer control of the system of FIG. 1 in providing interrelated interrupted drive and neuromuscular stimulation as illustrated by FIG. 2.

FIG. 3 shows a simplified flow chart for operation of the system of FIG. 1. In this particular embodiment, microcomputer 16 calculates the joint angles which correspond to the start and stop of carriage drive based upon the maximum flexion and maximum extension angle values and the T1 and T2 time interval values. If NMS stimulation is to be used in conjunction with carriage motion, microcomputer 16 also calculates the joint angles which correspond to the starts and stops of NMS excitation. As carriage 10 is moved, microcomputer 16 samples the joint angle as measured by angle sensor 32. As the angle sensed by angle sensor 32 changes, microcomputer 16 provides signals to clutch 14 and NMS output stage 18 provides the selected regimen of interrupted drive to carriage 10 and intermittent NMS stimulation.

Although the present invention has been described with reference to preferred embodiments, workers skilled in the art will recognize that changes may be made in form and detail without departing from the spirit and scope of the invention. For example, although the particular embodiment shown in FIG. 1 uses various analog inputs to select a program of interrupted drive and NMS stimulation, other forms of input to microcomputer 16 are also contemplated. For example, a user input/output device which includes a keyboard and display provides even greater flexibility in the form and content of input commands which can be provided to a microcomputer in order to establish a programmed interrupted drive/intermittent stimulation regimen.

What is claimed is:

1. Apparatus for moving a limb of a patient, the apparatus comprising:
   carriage means for supporting the limb through a range of reciprocal angular movement;
   drive means for providing drive force to cause movement of the carriage means between first and second positions;
   stimulation means for applying electrical stimulation to a muscle of the limb; and control means for coordinating operation of the drive means and the stimulation means so that alternating drive and pause periods are produced in which drive force is and is not provided by the drive means to the carriage means, respectively, as the carriage means is moved between the first and second positions, and so that the stimulation means applies electrical stimulation during stimulation periods which have a predetermined temporal relationship to the drive and pause periods.

2. The apparatus of claim 1 wherein the control means comprises:
means for providing a joint angle signal indicative of an angle of a joint of the limb;
means for selecting a duration $T1$ of the drive periods;
means for selecting a duration $T2$ of the pause periods;
means for selecting a time duration $T3$ of the NMS stimulation periods;
means for selecting a phase relationship $\phi$ between the NMS stimulation periods and the drive and pause periods; and
means for controlling the drive means and the NMS means as a function of $T1$, $T2$, $T3$, $\phi$, and the joint angle signal.

3. The apparatus of claim 2 wherein the drive means comprises a motor and a clutch.

4. The apparatus of claim 3 wherein the control means controls operation of the drive means by supplying a motor forward/reverse signal to the drive motor which selects the direction of movement of the drive motor.

5. The apparatus of claim 3 wherein the control means controls operation of the drive means by supplying a clutch ON/OFF signal which selects whether the drive motor is connected or disconnected from the carriage means.

6. A method of providing therapy to a patient comprising:
applying an interrupted drive force which passively moves a limb of the patient through a range of reciprocal angular movement between first and second positions, the interrupted drive force being produced by a series of alternating drive and pause periods; and
intermittently applying stimulation to selected muscles of the limb, the stimulation being applied to the muscles for stimulation periods having a predetermined phase relationship to the drive and pause periods.

7. Apparatus for moving a limb of a patient, comprising:
carriage means for supporting the limb through a range of reciprocal angular movement;
drive means for causing reciprocal angular movement of the carriage means between a flexion end position in which an angle of a joint of the limb is at a minimum, and an extension end position in which the angle is at a maximum;
angle sensing means for providing a joint angle signal representative of an angular position of the carriage means within the range of reciprocal angular movement; and
stimulation means for applying electrical stimulation to the limb;
means for selecting a program of alternating drive and pause periods of the drive means which characterize movement of the carriage means between the flexion and extension end positions during each operating cycle;
means for selecting a program of intermittent actuation of the stimulation means during each operating cycle; and
means for controlling the drive means and the stimulation means as a function of the joint angle signal and the selected programs of alternating drive and pause periods and of intermittent actuation.

8. Apparatus for providing therapy to a patient comprising:
carriage means for supporting a limb of the patient through a reciprocal range of angular movement between first and second positions; and
vibratory drive means for driving the carriage means along a path of movement between the first and second end positions and for superimposing vibratory motion in the direction of the path of movement upon the carriage means while the carriage means is driven between the first and second end positions.

9. The apparatus of claim 8 and further comprising:
means for applying stimulation to selected muscles of the limb in a predetermined temporal relationship to the vibratory motion.

10. Apparatus for moving a limb of a patient, the apparatus comprising:
carriage means for supporting the limb through a range of reciprocal angular movement;
drive means for providing drive force to the carriage means to cause reciprocal angular movement of the carriage means between first and second positions;
control means for controlling operation of the drive means to produce alternating drive and pause periods of the drive force supplied by the drive means to the carriage means as the carriage means is moved between the first and second positions;
means for selecting a duration $T1$ of the drive periods; and
means for selecting a duration $T2$ of the pause periods.

11. The apparatus of claim 10 and further comprising:
stimulation means for applying electrical stimulation to the muscles of limb; and
means for coordinating operation of the drive means and the stimulation means so that the stimulation means applies electrical stimulation during stimulation periods which have a predetermined temporal relationship to the drive and pause periods.

12. Apparatus for moving the limb of a patient, comprising:
carriage means for supporting the limb through a range of reciprocal angular movement between a flexion end position in which an angle of a joint of the limb is at a minimum, and an extension end position in which the angle is at a maximum;
drive means for supplying a drive force which causes movement of the carriage means between flexion and extension end positions; and
means for controlling the drive means to produce alternating drive and pause periods, the drive force being supplied to the carriage means during each drive period and not being supplied during each pause period as the carriage is moved between the flexion and extension end positions.

* * * * *